(12) United States Patent
Nam et al.

(10) Patent No.: US 7,756,645 B2
(45) Date of Patent: Jul. 13, 2010

(54) METHODS OF STORING, ALIGNING, AND RETRIEVING HAPLOTYPE DATA

(75) Inventors: Yun-sun Nam, Seoul (KR); Tae-jin Ahn, Seoul (KR)

(73) Assignee: Samsung Electronics Co., Ltd. (KR)

( * ) Notice: Subject to any disclaimer, the term of this patent is extended or adjusted under 35 U.S.C. 154(b) by 1460 days.

(21) Appl. No.: 11/008,032

(22) Filed: Dec. 9, 2004

(65) Prior Publication Data

US 2005/0250124 A1 Nov. 10, 2005

(30) Foreign Application Priority Data

Dec. 16, 2003 (KR) .................... 10-2003-0091867

(51) Int. Cl.
*G06F 19/00* (2006.01)
(52) U.S. Cl. ........................................ 702/20
(58) Field of Classification Search .............. 702/20
See application file for complete search history.

(56) References Cited

U.S. PATENT DOCUMENTS

2004/0267458 A1* 12/2004 Judson et al. ................. 702/20

FOREIGN PATENT DOCUMENTS

| JP | 2002-049628 | 2/2002 |
| JP | 2003228565 | 8/2003 |
| JP | 2003256433 | 9/2003 |
| WO | WO 02/086161 | 10/2002 |

OTHER PUBLICATIONS

R.E. Targan, Data Structures and Network Algorithms, SIAM, 1983, Chapter 4, pp. 45-57.
"C Magazine", vol. 3, No. 2 (1991).
vol. 34, No. 1 (1993).
Japanese Office Action—English and Japanese Versions for Patent Application No. 2004-364154; Date of Office Action: Nov. 29, 2004.
Gondo, Yoshiyuki; "Introduction to Algorithm and Data Structure", Chapter 8, Balanced Tree; C Magazine, Softbank Co, Ltd.;vol. 3, No. 2; pp. 66-74; Feb. 1, 1991 (article and English summary of relevance submitted in IDS of Apr. 3, 2006).
Aoe, Junichi; "Search Tree Method and Application Thereof"; Information Processing, Information Processing Society; vol. 34, No. 1; pp. 106-113; Jan. 15, 1993 (article and English summary of relevance submitted in IDS of Apr. 3, 2006).
Korean Office Action dated Jul. 25, 2005 for Application No. 10-2003-0091867.

\* cited by examiner

*Primary Examiner*—Jerry Lin
(74) *Attorney, Agent, or Firm*—Cantor Colburn LLP

(57) ABSTRACT

Provided are methods of storing, aligning, and retrieving haplotype data. A method of storing the haplotype data includes: determining the order of alleles in each single nucleotide polymorphism position of the haplotype data; aligning the haplotype data according to the order; and storing the aligned haplotype data in a predetermined data structure.

8 Claims, 3 Drawing Sheets

METHODS OF STORING, ALIGNING, AND RETRIEVING HAPLOTYPE DATA

This application claims the priority of Korean Patent Application No. 2003-91867, filed on Dec. 16, 2003, in the Korean Intellectual Property Office, the disclosure of which is incorporated herein in its entirety by reference.

BACKGROUND OF THE INVENTION

1. Field of the Invention

The present invention relates to methods of storing, aligning, and retrieving haplotype data, and more particularly, to methods of storing haplotype data by ordering and aligning them during storing the haplotype data in a database, and retrieving them thereafter.

2. Description of the Related Art

Haplotype data as a deoxyribonucleic acid (DNA) sequence are a set of single nucleotide polymorphism (SNP) alleles existing along chromosome regions. The SNP indicates DNA base variations specifying individualities, and about one of thousand bases appears in the human genome. For example, if human chromosomes contain 30% of adenines (A) and 70% of guanines (G) at the corresponding SNP, the A and G are called variants or alleles of the corresponding SNP.

For example, assume that haplotype data of three people have the following base array, respectively:

```
ATAGTCACGTACGTATTACG;
(SEQ ID NO.:1)

ATCGTCACGAACGTATGACG;
(SEQ ID NO.:2)
and

ATCGTCACGAACGTATGACG,
(SEQ ID NO.:3)
``` where C denotes cytosine, and T denotes thymine.

In this case, the SNP set corresponds to a third, tenth, and seventeenth position. Thus, the alleles in the third, tenth, and seventeenth positions are A/C, T/A, and T/G, respectively.

Conventionally, such haplotype data are stored in a list type data structure. However, in order to examine if there is a certain haplotype data or to extract related information corresponding to the certain haplotype data if the certain haplotype data is determined to exist, the list data structure requires O(n) time for the search, where n is the number of haplotype data in the database. Therefore, it is necessary to provide methods of storing and aligning the haplotype data by which the search time can be reduced.

SUMMARY OF THE INVENTION

The present invention provides methods of storing, aligning, and retrieving haplotype data efficiently, for providing an alignment order to the haplotype data to store them in a binary tree data structure.

According to an aspect of the present invention, there is provided a method of storing haplotype data, the method comprising: determining the order of alleles in each simple nucleotide polymorphism (SNP) position of the haplotype data; aligning the haplotype data according to the order; and storing the aligned haplotype data in a predetermined data structure.

According to another aspect of the present invention, there is provided a method of aligning haplotype data, the method comprising: determining the order of alleles in each SNP position of the haplotype data; allocating integers to the alleles according to the order of the alleles for each SNP position; substituting the alleles contained in each haplotype data with the allocated integers; numerating integer sequences corresponding to each haplotype data according to position values; and aligning the haplotype data based on the magnitudes of numbers corresponding to each haplotype data.

According to still another aspect of the present invention, there is provided a method of retrieving haplotype data by determining the order of alleles in SNP positions of the haplotype data, numerating the haplotype data according to the order, and retrieving the haplotype data in a database storing the haplotype data in a predetermined data structure by using the numerated values, the method comprising: determining the order of the alleles consisting of the sample haplotype data in the same manner as the order of alleles in each SNP position of the haplotype data stored in the database; allocating integers to the alleles according to the order of the alleles; substituting the alleles of the sample haplotype data with the allocated integers; numerating the substituted integers according to position values; and retrieving the database by using the numerated values according to the data structure.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
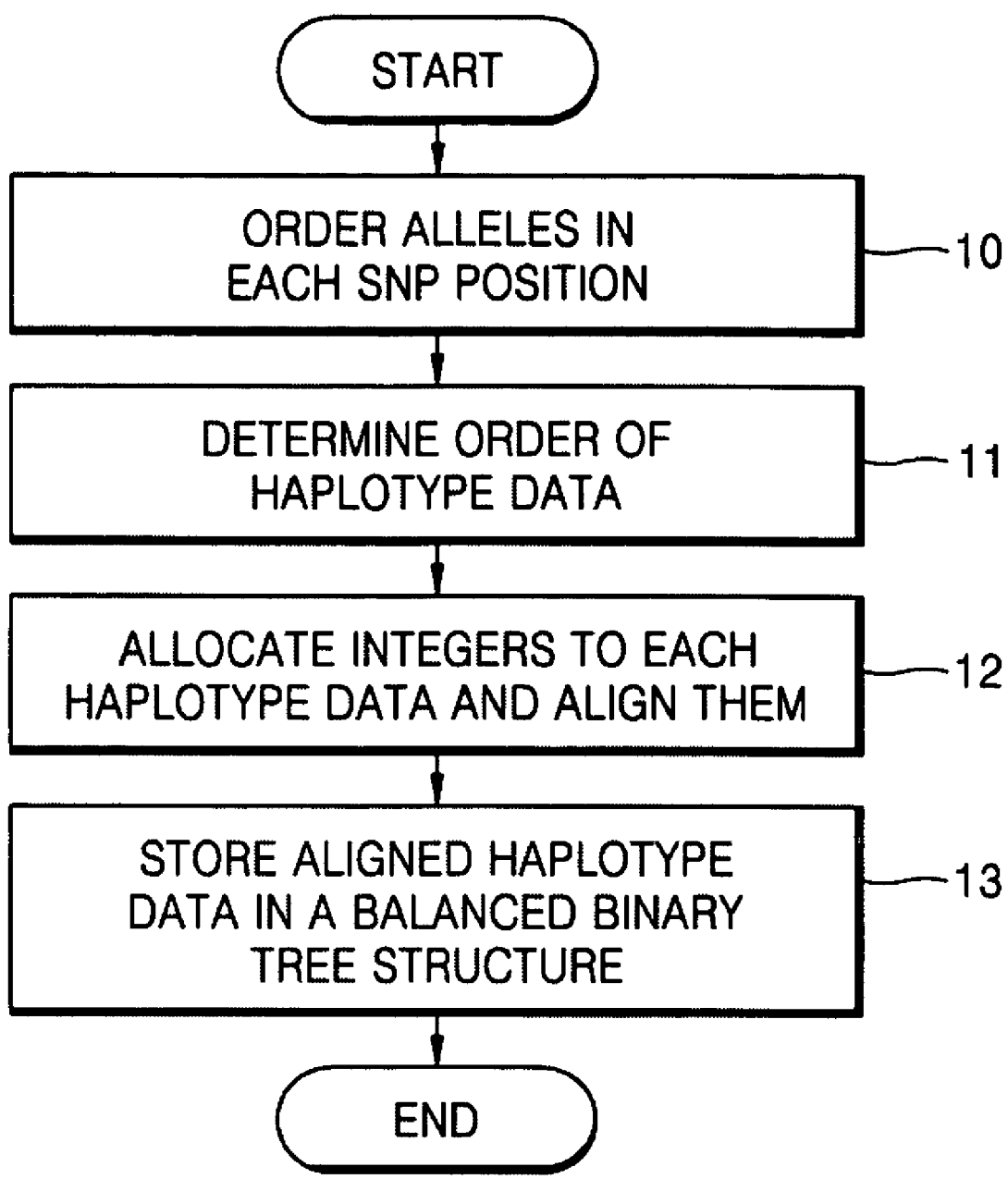
FIG. 1 is a flow chart showing a method of storing haplotype data according to the present invention.

The present invention will now be described more fully with reference to the accompanying drawings, in which exemplary embodiments of the invention are shown.

The invention may, however, be embodied in many different forms and should not be construed as being limited to the embodiments set forth herein; rather, these embodiments are provided so that this disclosure will be thorough and complete, and will fully convey the concept of the invention to those skilled in the art. Like reference numerals in the drawings denote like elements, and thus their description will not be repeated.

According to the present invention, the haplotype data are stored in a balanced binary tree data structure, which has been disclosed in "*R. E. Tarjan, Data Structures and Network Algorithms, SIAM, 1983.*"

To store the haplotype data in a balanced binary tree data structure, it is necessary to align corresponding data. FIG. 1 is a flow chart showing a method of aligning and storing the haplotype data according to the present invention.

First, alleles in each single nucleotide polymorphism (SNP) position are aligned (operation 10) in a predetermined order. For example, if the SNP has three types of alleles, A, T, and G, they are arbitrarily ordered, and the result will be one of six orders: A<T<G, A<G<T, T<A<G, T<G<A, G<T<A, G<A<T.

The following table shows an example where the alleles corresponding to each SNP position are differently ordered.

TABLE 1

| SNP POSITION | ALLELES |
|---|---|
| 1 | A < G < C |
| 2 | A < T |
| 3 | T < C < A |
| 4 | T < C |
| 5 | T < G < C < A |
| 6 | G < C |
| 7 | T < C |
| 8 | A < G < C < T |
| 9 | A < G |
| 10 | T < G |

The magnitudes of the haplotype data are compared with each other in order of the alleles in each SNP position, and the order of the haplotype data is determined (operation 11). The magnitude comparison is accomplished by comparing the magnitude of the alleles in an SNP position where alleles become differed for the first time starting from the first SNP position. In other words, for two haplotype data, $HX=(x_1, x_2, \ldots, x_n)$, $HY=(y_1, y_2, \ldots, y_n)$, if it is set that $x_1=y_1, x_2=y_2, x_{i-1}=y_{i-1}$, and $x_i < y_i$ in ith position, the result of the magnitude comparison becomes HX<HY. For example, if two haplotype data, HX=(A, A, T, C, G, C, C, G, G, G), HY=(A, A, C, T, T, G, T, A, A, T), are provided, it is recognized that there is a difference in the third position for the first time, that is, T and C, respectively. According to the Table 1, since T<C in the third SNP position, HX<HY is resulted.

Integers are allocated to each haplotype data according to the determined order of the haplotype data (operation 12). The integers of 0, 1, ..., q are allocated based on the order or the alleles in each SNP position. Here, q denotes the number of alleles in the corresponding SNP position minus 1.

For example, if the order of alleles is determined as shown in Table 1, integers are allocated to each allele in each SNP position as shown in the following table.

TABLE 2

| SNP POSITION | ALLELES | INTEGERS |
|---|---|---|
| 1 | A < G < C | A = 0, G = 1, C = 2 |
| 2 | A < T | A = 0, T = 1 |
| 3 | T < C < A | T = 0, C = 1, A = 2 |
| 4 | T < C | T = 0, C = 1 |
| 5 | T < G < C < A | T = 0, G = 1, C = 2, A = 3 |
| 6 | G < C | G = 0, C = 1 |
| 7 | T < C | T = 0, C = 1 |
| 8 | A < G < C < T | A = 0, G = 1, C = 2, T = 3 |
| 9 | A < G | A = 0, G = 1 |
| 10 | T < G | T = 0, G = 1 |

Then, each haplotype data is substituted with an integer sequence based on integers allocated to the alleles. After completing the substitution, the substituted integer sequences are converted into integer values based on position values of the substituted integers. The position values are determined by setting an end position as 1 and then multiplying a just previous position value by the number of alleles in the just previous SNP position as the position number is incremented from the end position. For example, the case shown in Table 2 will be converted into the following Table 3.

TABLE 3

| SNP POSITION | NUMBER OF ALLELES | POSITION VALUE |
|---|---|---|
| 1 | 3 | 2 x 2 x 4 x 2 x 2 x 4 x 2 x 3 x 2 = 3072 |
| 2 | 2 | 2 x 2 x 4 x 2 x 2 x 4 x 2 x 3 = 1536 |
| 3 | 3 | 2 x 2 x 4 x 2 x 2 x 4 x 2 = 512 |
| 4 | 2 | 2 x 2 x 4 x 2 x 2 x 4 = 256 |
| 5 | 4 | 2 x 2 x 4 x 2 x 2 = 64 |
| 6 | 2 | 2 x 2 x 4 x 2 = 32 |
| 7 | 2 | 2 x 2 x 4 = 16 |
| 8 | 4 | 2 x 2 = 4 |
| 9 | 2 | 2 |
| 10 | 2 | 1 |

For example, a sequence of haplotype data, (C, T, C, T, G, G, C, C, A, T), is substituted to an integer sequence, (2,1,1,0,1,0,1,2,0,0), according to Table 2, and then the integer sequence is converted into an integer value, 8280 (2×3072+1×1536+1×512+0×256+1×64+0×32+1×16+2×4+0×2+0×1= 8280), according to Table 3.

Through such calculation, all the haplotype data are converted into integer values. The following table shows an example where each haplotype data are converted into integer values according to Table 3.

TABLE 4

| NUMBER | HAPLOTYPE DATA | INTEGER |
|---|---|---|
| 1 | C,T,C,T,G,G,C,C,A,T | 8280 |
| 2 | A,T,A,C,T,C,T,G,G,T | 2854 |
| 3 | A,T,T,C,C,G,C,T,A,T | 1948 |
| 4 | A,T,T,C,T,G,T,A,G,G | 1795 |
| 5 | A,T,T,C,T,G,T,A,G,T | 1794 |
| 6 | G,T,A,C,A,G,C,C,A,T | 3544 |
| 7 | G,A,T,C,T,G,C,C,A,T | 3348 |
| 8 | G,A,A,C,T,G,T,A,G,G | 4355 |
| 9 | G,T,C,C,T,G,C,G,A,T | 5396 |
| 10 | G,T,C,T,G,G,C,G,A,T | 5204 |
| 11 | C,T,T,C,C,C,T,G,G,T | 8102 |
| 12 | G,T,T,C,G,G,C,G,A,T | 4948 |
| 13 | G,T,T,C,T,C,T,G,A,T | 4900 |
| 14 | G,T,C,T,A,G,C,T,A,T | 5340 |
| 15 | C,T,A,C,T,G,C,G,A,T | 8980 |
| 16 | G,T,T,C,T,G,T,G,A,T | 4868 |

TABLE 4-continued

| NUMBER | HAPLOTYPE DATA | INTEGER |
|---|---|---|
| 17 | G,T,T,T,T,G,C,G,A,T | 4628 |

The haplotype data are stored in a balanced binary tree structure by using corresponding integer values (operation 13). The integer values corresponding to each haplotype data are allocated to a key value of each node in the balanced binary tree structure. In addition, for the node x, the haplotype data having a key value smaller than that of x is stored to a node in a left sub-tree, and the haplotype data having a key value larger than the one of x is stored to a node in a right sub-tree. In addition to the haplotype data and the key value, information on the corresponding haplotype data, e.g., a frequency indicating a proportion of subjects having corresponding haplotype data in a particular population, may be stored for each node.

Figure 2:
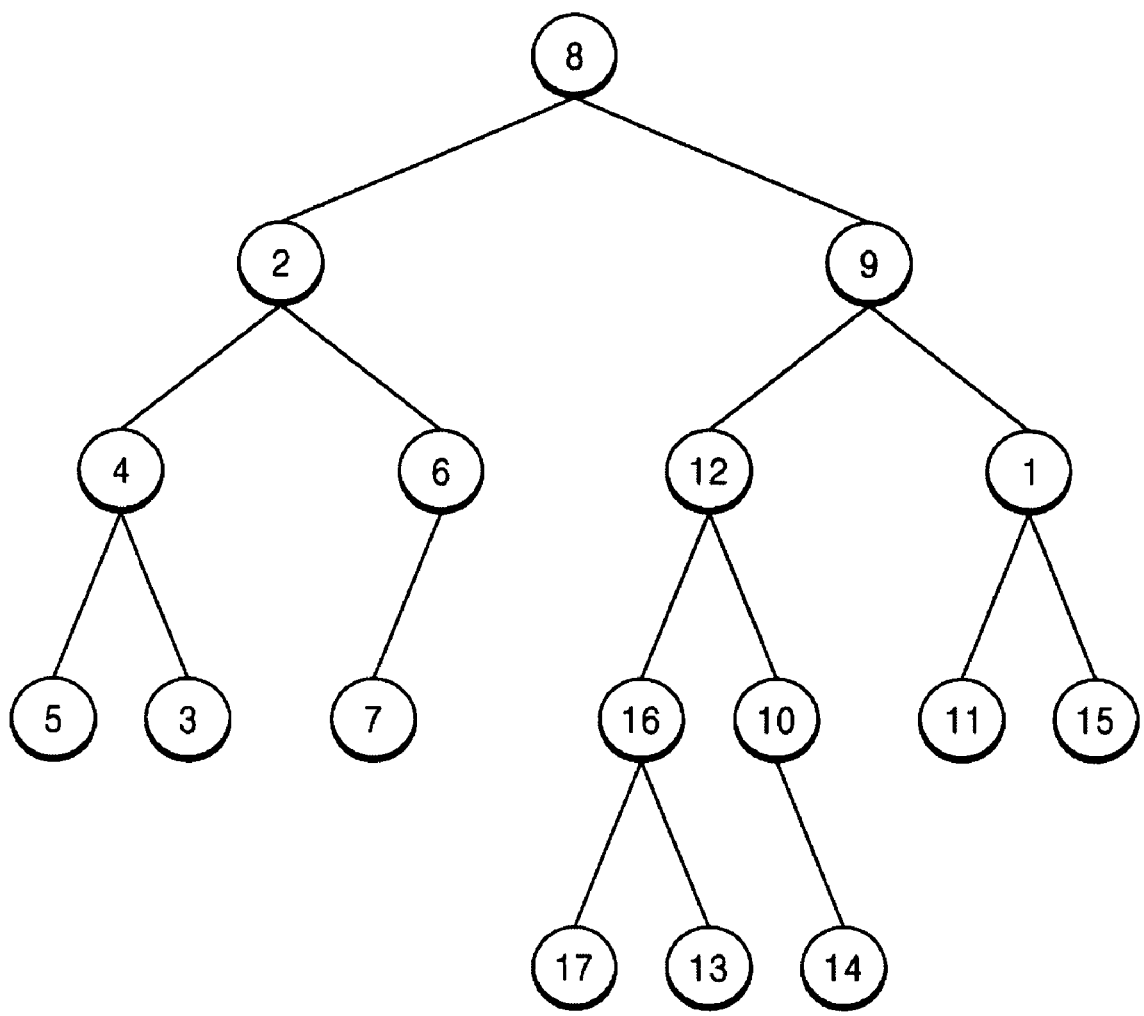
FIG. 2 is a tree diagram showing that the haplotype data shown in Table 4 are stored in a balanced binary tree structure.

FIG. 2 shows an example where the haplotype data in Table 4 are stored in a balanced binary data structure. In the shown balanced binary data structure, the integer value corresponding to each number of Table 4 is designated as a key value of each node. For example, the integer value of the haplotype data stored in the node number 2 is 2854, and the haplotype data of the node number 4 having a smaller key value than that of the node number 2 is stored in the left sub-tree of the node of number 2. In addition, the haplotype data of the node number 6 having a larger key value than that of the node number 2 is stored in the right sub-tree of the node of number 2.

Figure 3:
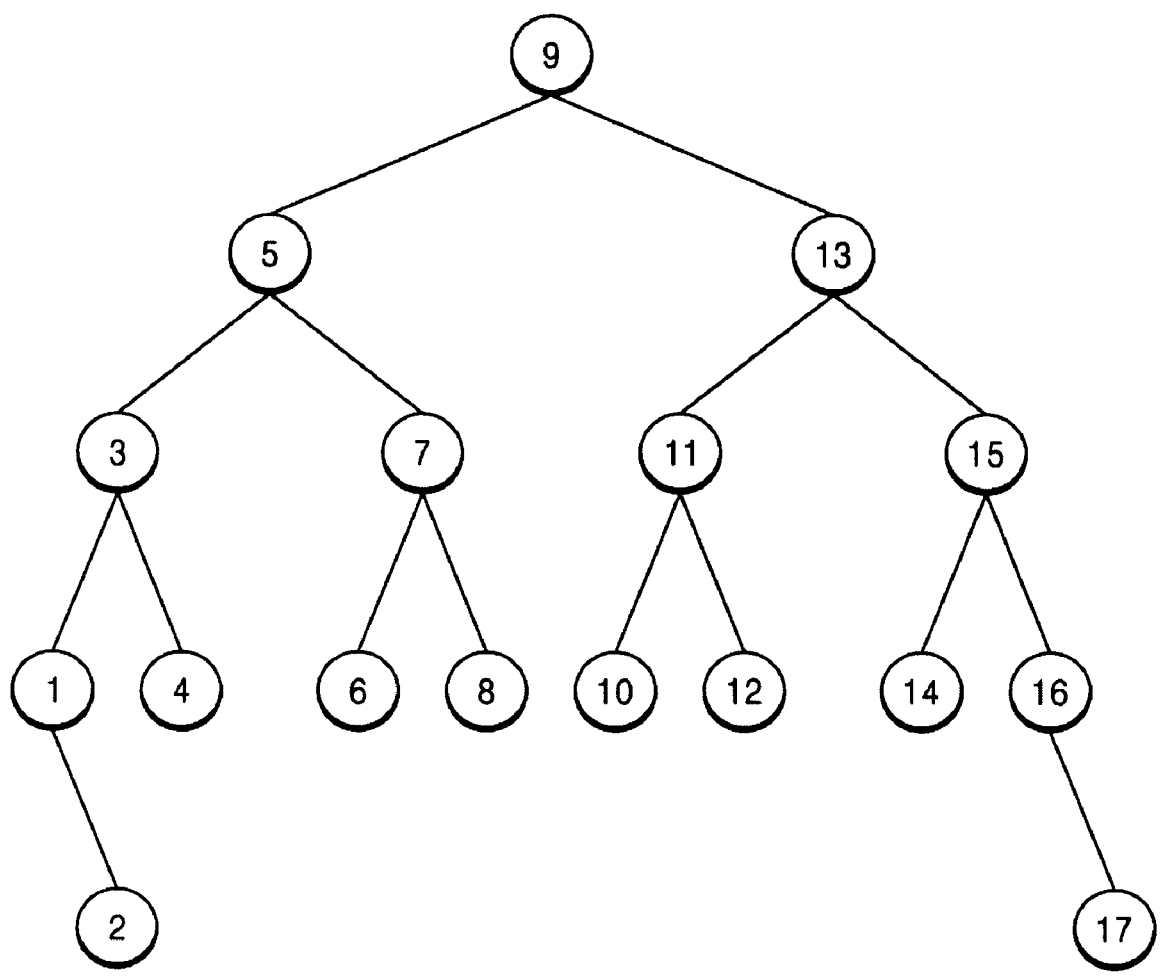
FIG. 3 is a tree diagram showing that the haplotype data shown in Table 5 are stored in a balanced binary tree structure.

FIG. 3 shows another example where the haplotype data are stored in a balanced binary data structure according to another embodiment of the present invention. The tree structure is based on the result of aligning the haplotype data according to their magnitudes when the alleles have the order of A<C<G<T as shown in the following table.

TABLE 5

| NUMBER | HAPLOTYPE DATA | FREQUENCY | | |
|---|---|---|---|---|
| | | TOTAL | AFRICAN | EUROPEAN |
| 1 | A,T,C,T,T,G,C,G,A,T | 0.064 | 0.021 | 0.109 |
| 2 | A,T,T,C,T,C,T,G,G,T | 0.011 | 0.021 | 0 |
| 3 | A,T,T,C,T,G,C,G,A,T | 0.011 | 0 | 0.022 |
| 4 | A,T,T,C,T,G,T,A,G,G | 0.362 | 0.208 | 0.522 |
| 5 | A,T,T,C,T,G,T,A,G,T | 0.011 | 0.021 | 0 |
| 6 | G,A,T,C,G,G,C,G,A,T | 0.021 | 0.042 | 0 |
| 7 | G,A,T,C,T,G,C,G,A,T | 0.021 | 0.042 | 0 |
| 8 | G,A,T,C,T,G,T,A,G,G | 0.011 | 0.021 | 0 |
| 9 | G,T,C,C,T,G,C,G,A,T | 0.011 | 0 | 0.022 |
| 10 | G,T,C,T,G,G,C,G,A,T | 0.011 | 0.021 | 0 |
| 11 | G,T,T,C,G,C,T,G,G,T | 0.011 | 0.021 | 0 |
| 12 | G,T,T,C,G,G,C,G,A,T | 0.011 | 0.021 | 0 |
| 13 | G,T,T,C,G,G,T,A,G,T | 0.011 | 0.021 | 0 |
| 14 | G,T,T,C,T,C,T,G,A,T | 0.032 | 0.062 | 0 |
| 15 | G,T,T,C,T,G,C,G,A,T | 0.138 | 0.271 | 0 |
| 16 | G,T,T,C,T,G,T,G,A,T | 0.043 | 0.083 | 0 |
| 17 | G,T,T,T,T,G,C,G,A,T | 0.011 | 0 | 0.022 |

In Table 5, each node corresponding to each number has a frequency in each sample population as information on each haplotype data.

Since the haplotype data stored in a balanced binary tree structure has a tree depth of (Dog n), it is possible to ensure a fast search in comparison with the conventional art. For example, if it is necessary to identify whether a test haplotype data, $H_{test}$=(G, T, T, C, G, G, C, G, A, T), in the tree structure in FIG. 3 has been already known, an integer value corresponding to the haplotype data, $H_{test}$=(G, T, T, C, G, G, C, G, A, T), is calculated based on the condition A<C<G<T and the method illustrated in Tables 1 through 4. The calculated integer value is compared with a key value of the first node of number 9 to determine which is larger. As a result of the determination, if the calculated integer value is larger, the calculated integer value is compared with a key value of the node number 13 positioned in the right sub-tree. Otherwise, it is compared with a key value of the node number 5 positioned in the left sub-tree to determine which is larger, again. After the search using such a method, it is possible to identify whether the test haplotype data has been already known through a maximum of three comparisons.

The methods of storing, aligning, and retrieving haplotype data according to the invention can also be embodied as computer readable codes on a computer readable recording medium. The computer readable recording medium is any data storage device that can store data which can be thereafter read by a computer system.

Examples of the computer-readable recording medium include read-only memory (ROM), random-access memory (RAM), CD-ROMs, magnetic tapes, floppy disks, optical data storage devices, and carrier waves (such as data transmission through the Internet). The computer readable recording medium can also be distributed over network-coupled computer systems so that the computer-readable code is stored and executed in a distributed fashion.

According to the present invention, integer numbers are allocated to n haplotype data, the integer numbers are aligned, and the aligned haplotype data are stored in a balanced binary tree structure, so that a subsequent search lapses O(log n)

time, which is smaller than O(n) times of the conventional art. Therefore, it is possible to achieve a fast search. In addition, the fast search allows various research groups to readily compare and exchange the haplotype data.

While the present invention has been particularly shown and described with reference to exemplary embodiments thereof, it will be understood by those skilled in the art that various changes in form and details may be made therein without departing from the spirit and scope of the invention as defined by the appended claims. The exemplary embodiments should be considered in descriptive sense only and not for purposes of limitation. Therefore, the scope of the invention is defined not by the detailed description of the invention but by the appended claims, and all differences within the scope will be construed as being included in the present invention.

What is claimed is:

1. A method of storing haplotype data, the method comprising:

determining an order of all alleles for each single nucleotide polymorphism (SNP) position of each haplotype data in a plurality of haplotype data;

allocating an integer to each allele of each single nucleotide polymorphism position according to the determined order of the alleles;

substituting the allocated integer for the allele of each SNP position contained in each haplotype data;

calculating an integer value corresponding to each haplotype data, wherein the integer value for a haplotype data is the sum over all SNP positions of the haplotype data of the allocated integer for the allele at a SNP position times a position value for the SNP position;

aligning the haplotype data according to magnitude of the calculated integer value of each haplotype data; and storing the aligned haplotype data in a data structure to a database;

wherein the method is executed by a suitably-programmed computer.

2. The method according to claim 1, wherein the integers are allocated to the ordered alleles of the single nucleotide polymorphism (SNP) in an incrementing manner from 0 to the number of alleles minus 1.

3. The method according to claim 1, wherein the data structure is a balanced binary tree structure.

4. The method according to claim 3, wherein the integer value for each haplotype data is stored in the balanced binary tree structure as a key value of each node.

5. The method according to claim 4, wherein a node for a haplotype data further stores additional information on the haplotype data besides the key value.

6. The method of claim 1, further comprising:

substituting an allele of each SNP position of a test haplotype data with the allocated integer;

calculating an integer value for the test haplotype data, wherein the integer value is the sum over all SNP positions of the test haplotype data of the allocated integer for the allele at a SNP position times a position value for the SNP position; and determining if the test haplotype data is a stored haplotype data by comparing the integer value of the test haplotype data with the integer values of stored haplotype data.

7. The method according to claim 6, further comprising when the test haplotype data is determined to be a stored haplotype data,
retrieving the stored haplotype data with an integer value identical to the integer value of the test haplotype data.

8. The method of claim 1,
wherein a number of SNP positions in a haplotype data is n and a number of alleles for the nth SNP position is Xn, and
wherein a position value for each SNP position is calculated by setting the position value of the $n^{th}$ SNP to 1, the position value of the (n−1)th SNP is $(1 \cdot X_n)$, the position value of the (n−2)th SNP is $(1 \cdot X_n \cdot X_{n-1})$, the position of the (n−3)th SNP is and the position value of the $1^{st}$ SNP is $(1 \cdot X_n \cdot X_{n-1} \cdot X_{n-2} \ldots X_{n-(n-1)})$.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial
<220> FEATURE:
<223> OTHER INFORMATION: synthetic construct

<400> SEQUENCE: 1
atagtcacgt acgtattacg                                              20

<210> SEQ ID NO 2
<211> LENGTH: 20
<212> TYPE: DNA
<213> ORGANISM: Artificial
<220> FEATURE:
<223> OTHER INFORMATION: synthetic construct

<400> SEQUENCE: 2
atcgtcacga acgtatgacg                                              20

<210> SEQ ID NO 3
<211> LENGTH: 20
<212> TYPE: DNA
<213> ORGANISM: Artificial
<220> FEATURE:
<223> OTHER INFORMATION: synthetic construct

<400> SEQUENCE: 3
atcgtcacga acgtatgacg                                              20
```